(12) United States Patent
Ser et al.

(10) Patent No.: US 10,368,804 B2
(45) Date of Patent: Aug. 6, 2019

(54) DEVICE, SYSTEM AND METHOD FOR DETECTION OF FLUID ACCUMULATION

(71) Applicant: Nanyang Technological University, Singapore (SG)

(72) Inventors: Wee Ser, Singapore (SG); Feng Yang, Singapore (SG); Junfeng Yu, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 559 days.

(21) Appl. No.: 14/421,505

(22) PCT Filed: Aug. 14, 2013

(86) PCT No.: PCT/SG2013/000345
§ 371 (c)(1),
(2) Date: Feb. 13, 2015

(87) PCT Pub. No.: WO2014/027962
PCT Pub. Date: Feb. 20, 2014

(65) Prior Publication Data
US 2015/0190091 A1 Jul. 9, 2015

Related U.S. Application Data

(60) Provisional application No. 61/682,992, filed on Aug. 14, 2012.

(51) Int. Cl.
*A61B 5/00* (2006.01)
*A61B 7/04* (2006.01)
*G06K 9/00* (2006.01)

(52) U.S. Cl.
CPC ............ *A61B 5/4875* (2013.01); *A61B 5/726* (2013.01); *A61B 5/7225* (2013.01);
(Continued)

(58) Field of Classification Search
None
See application file for complete search history.

(56) References Cited

U.S. PATENT DOCUMENTS

| 8,532,360 B2 * | 9/2013 | Suri | A61B 8/0891 |
| | | | 382/131 |
| 2003/0087456 A1 * | 5/2003 | Jones | A61B 5/0059 |
| | | | 436/171 |

(Continued)

FOREIGN PATENT DOCUMENTS

| WO | 2006/113968 A1 | 11/2006 |
| WO | 2008/024624 A2 | 2/2008 |
| WO | 2009/020571 A1 | 2/2009 |

OTHER PUBLICATIONS

International Search Report and Written Opinion from International Patent Application No. PCT/SG2013/000345, dated Nov. 25, 2013.

(Continued)

*Primary Examiner* — Matthew Kremer
(74) *Attorney, Agent, or Firm* — Merchant & Gould P.C.

(57) ABSTRACT

A method of detecting a level of fluid accumulation in an internal organ of a subject is proposed, as well as a system for carrying out the method. The method comprises: providing at least one classifier trained to distinguish between two or more levels of fluid accumulation; acquiring an audio signal (110) generated by said internal organ; and processing, using at least one processor (134), said audio signal (110) by: performing feature extraction to generate at least one feature vector from the audio signal; and assigning a fluid level from the two or more levels to the audio signal by passing the at least one feature vector to the at least one classifier.

20 Claims, 8 Drawing Sheets (52) U.S. Cl.
CPC .......... *A61B 5/7267* (2013.01); *A61B 5/7275* (2013.01); *A61B 5/7278* (2013.01); *A61B 7/04* (2013.01); *G06K 9/00496* (2013.01); *A61B 2560/0475* (2013.01); *A61B 2562/0204* (2013.01); *G06K 2209/05* (2013.01)

(56) References Cited

U.S. PATENT DOCUMENTS

| | | | |
|---|---|---|---|
| 2004/0142496 A1* | 7/2004 | Nicholson | A61B 5/055 436/536 |
| 2006/0047215 A1* | 3/2006 | Newman | A61B 5/0002 600/513 |
| 2007/0276270 A1 | 11/2007 | Tran | |
| 2008/0082017 A1* | 4/2008 | Savic | A61B 7/003 600/529 |
| 2008/0183096 A1* | 7/2008 | Snyder | G06K 9/00496 600/545 |
| 2009/0036777 A1* | 2/2009 | Zhang | A61B 5/0031 600/459 |
| 2010/0100001 A1* | 4/2010 | Aguilar | A61B 3/113 600/544 |
| 2011/0009746 A1* | 1/2011 | Tran | A61B 8/08 600/437 |
| 2012/0259803 A1* | 10/2012 | Whitlow | A61B 5/16 706/20 |

OTHER PUBLICATIONS

S. Charleston-Villalobos et al.: "Assessment of multichannel lung sounds parameterization for two-class classification in interstitial lung disease patients", Computers in Biology and Medicine, vol. 41, Issue 7, Jul. 2011, pp. 473-482.

Zumray Dokur: "Respiratory sound classification by using an incremental supervised neural network", Pattern Analysis and Applications, vol. 12, Issue 4, Dec. 2009, pp. 309-319.

Hugh M. Kinghorn, M.D.: "The Classification of Rales", The Canadian Medical Association Journal, vol. 26, Issue 4, Apr. 1932, pp. 438-445.

Mete Yeginer et. al.: "Feature extraction for pulmonary crackle representation via wavelet networks", Computers in Biology and Medicine, vol. 39, Issue 8, Aug. 2009, pp. 713-721.

Kemper et al., "Digital Holographic Microscopy for Live Cell Applications and Technical Inspection," Applied Optics, vol. 47, No. 4, Feb. 1, 2008, pp. A52-A61.

Waller et al., "Transport of Intensity Phase Imaging in a Volume Holographic Microscope," Optics Letters, vol. 35, No. 17, Sep. 1, 2010, pp. 2961-2963.

* cited by examiner (a) Portable device configuration (b) Sensor-computer configuration (c) Sensor-cloud computing configuration

DEVICE, SYSTEM AND METHOD FOR DETECTION OF FLUID ACCUMULATION

This application is a National Stage Application of PCT/SG2013/000345, filed 14 Aug. 2013, which claims benefit of U.S. Provisional Ser. No. 61/682,992, filed 14 Aug. 2012 and which applications are incorporated herein by reference. To the extent appropriate, a claim of priority is made to each of the above disclosed applications.

FIELD OF THE INVENTION

This invention relates to a system and a method for detecting fluid accumulation in internal organs, for example in the lungs, in non-invasive fashion.

BACKGROUND OF THE INVENTION

Heart failure is highly prevalent in many countries in the world and is the primary reason for hospital admissions. A major complication for patients with moderate-to-severe heart failure is accumulation of excess fluids in the lungs. Excess lung fluid is a frequent cause of hospital re-admissions. In fact, it has been reported that by the time excess lung fluid is detected, it is often too late to avert hospitalization.

Previously proposed methods of lung fluid detection include the use of X-ray imaging, CT scan (of the thorax), and measurement of serum biomarkers (e.g. Brain Natriuretic Peptide). These methods are sophisticated and can involve the use of bulky equipment or can take a long time to produce a measurement, thus making them impractical for use during an emergency or outside a hospital environment.

A less sophisticated and faster method of assessing accumulation of excess lung fluid is for a physician to perform auscultation (i.e. listening for audible evidence of fluid accumulation) using a stethoscope. However, while quicker and simpler, this method lacks the sensitivity of the more sophisticated methods discussed above.

A more recent development is a device which can be implanted in order to continuously monitor the fluid status of the lungs, for example by measuring intrathoracic impedance. Although this may advantageously allow earlier detection of fluid accumulation, implantation is an invasive procedure.

There is a need for a non-invasive approach to the detection of fluids in internal organs such as lungs.

SUMMARY OF THE INVENTION

In general terms, the present invention proposes a method for detecting fluid accumulation in an internal organ of a subject. The method acquires an audio signal generated by the internal organ and processes the signal to automatically detect, using a trained classifier, the level of fluid accumulation in the internal organ.

In a first aspect, the present invention provides a method of detecting a level of fluid accumulation in an internal organ of a subject, comprising:
  providing at least one classifier trained to distinguish between two or more levels of fluid accumulation;
  acquiring an audio signal generated by said internal organ; and
  processing said audio signal by:
    performing feature extraction to generate at least one feature vector from the audio signal;
    assigning a fluid level from the two or more levels to the audio signal by passing the at least one feature vector to the at least one classifier.

The levels may be presence of fluid and absence of fluid.

In certain embodiments, said audio signal is segmented into consecutive time windows, and a feature vector is generated for each time window. The consecutive time windows may at least partially overlap.

In certain embodiments, selected components of each feature vector are passed to the at least one classifier.

Each feature vector may be passed to the or each said classifier, to generate a plurality of tentative fluid levels for the audio signal; and said assigning may comprise selecting the most frequent level from amongst the plurality of tentative fluid levels.

In certain embodiments, the feature extraction comprises performing one or more of the following on the audio signal: determining mel-frequency cepstral coefficients; determining perceptual linear prediction coefficients; determining linear prediction coefficients; or determining coefficients of a wavelet transform.

The at least one classifier may comprise at least one linear classifier and/or may comprise at least one non-linear classifier.

The method may further comprise training the or each said classifier. For example, said training may comprise:
  acquiring audio signals from a plurality of subjects having known levels of fluid accumulation;
  performing feature extraction on the audio signals to generate a plurality of feature vectors; and
  performing feature selection on the plurality of feature vectors to identify one or more components of the feature vectors which are useful for discriminating between the two or more levels.

Feature selection may be performed by identifying the N most important features from the feature vectors. The importance of a feature may be calculated according to:

$$I(x_i) = \frac{\sum_{j \neq k} (m_{i,c(j)} - m_{i,c(k)})^2}{\sum_{c(j)} \sigma_{i,c(j)}^2},$$

where $i=1, \ldots, M$; $M$ is the dimension of each feature vector; $m_{i,c(j)}$ and $\sigma_{i,c(j)}^2$ are the sample mean and variance respectively of the feature $x_i$ for the class $c(j)$; $c(j)$, $j=1, 2, \ldots N_c$ is the $j^{th}$ class; and $N_c$ is the number of levels of fluid accumulation.

In certain embodiments, said acquiring comprises positioning at least one sensor on the subject or subjects in proximity to said internal organ such that the sensor is acoustically coupled to the internal organ:

In a second aspect, the present invention provides a system for detecting a level of fluid accumulation in an internal organ of a subject, comprising:
  at least one sensor positionable on the subject to measure an audio signal from said internal organ;
  a memory configured to store data representing the audio signal; and
  at least one processor in communication with the memory and being configured to:
    retrieve, from said memory, data representing at least one classifier trained to distinguish between two or more levels of fluid accumulation;

process said audio signal by performing feature extraction to generate at least one feature vector from the audio signal; and assign a fluid level from the two or more levels to the audio signal by passing the at least one feature vector to the at least one classifier.

In a third aspect, the present invention provides a system for detecting a level of fluid accumulation in an internal organ of a subject, comprising:

at least one sensor positionable on the subject to measure an audio signal from said internal organ; and at least one processor configured to perform the method of the first aspect of the invention.

In a fourth aspect, the present invention provides a computer-readable storage medium for detecting a level of fluid accumulation in an internal organ of a subject, the computer-readable storage medium having stored thereon:

data representing parameters of at least one classifier trained to distinguish between two or more levels of fluid accumulation; and instructions for causing at least one processor to:
retrieve data representing an audio signal generated by said internal organ; and
process the data representing said audio signal by:
performing feature extraction to generate at least one feature vector from the audio signal;
assigning a fluid level from the two or more levels to the audio signal by passing the at least one feature vector to the at least one classifier.

The invention may be defined as a method, as a system comprising a processor programmed to perform at least part of the method, or as software operative when run by a processor to perform at least part of the method.

BRIEF DESCRIPTION OF THE DRAWINGS

Embodiments of the invention will now be described, by way of non-limiting example only, with reference to the accompanying drawings in which.

DETAILED DESCRIPTION OF EMBODIMENTS

Embodiments of the present invention provide a means of detecting and/or monitoring fluid accumulation in lung and other internal organs within a short duration, automatically, and in a non-invasive manner.

Figure 1:
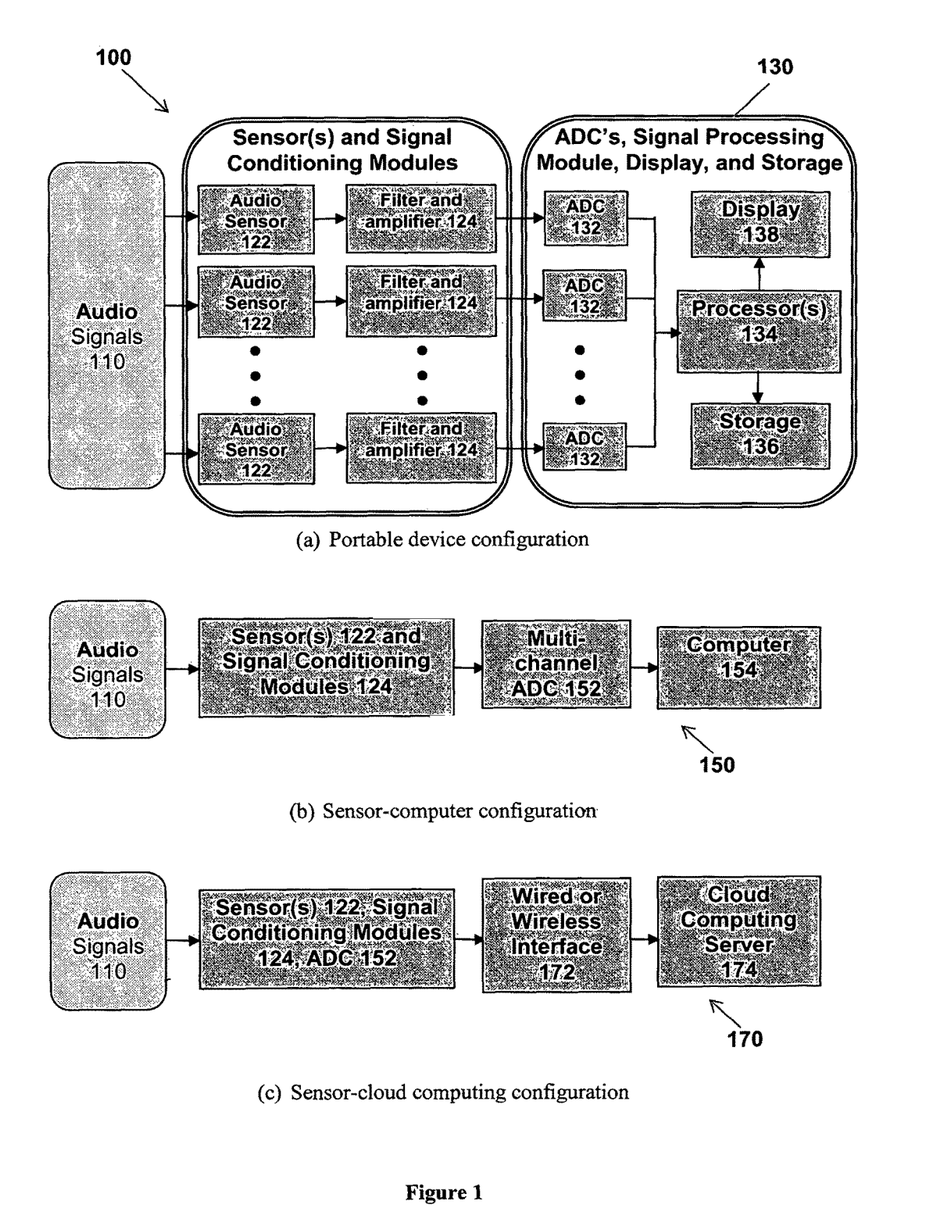
FIGS. 1(a) to 1(c) are functional block diagrams of systems according to embodiments of the present invention.

Referring initially to FIG. 1(a), an embodiment of a system 100 for detecting fluid accumulation in internal organs, especially (but not exclusively) lung, is shown. The system 100 comprises one or more acoustic sensor modules 122 to record lung sounds 110 from a patient. The lung sounds recorded by each sensor module 122 are converted to electrical signals and fed to a signal conditioning module 124 comprising a filter and an amplifier. Outputs of the signal conditioning modules 124 are digitized by analog to digital converters (ADC) 132 and are processed by a signal processing module 134 comprising one or more processors. The signal processing module 134 includes sub-modules 310-340 (FIG. 3) which carry out processes to enhance the signal quality and to decide if fluids are present in the lung of the patient. The ADCs 132 and signal processing module 134 may be contained within a housing of a portable monitoring device 130, for example. The portable monitoring device 130 may also have a display 138 and a non-volatile memory 136, each of which are coupled to the signal processing module 134, either directly or via a bus.

FIG. 1(b) shows an alternative configuration of a system 150 in which, similarly to the embodiment of FIG. 1(a), audio 110 is received by audio sensors 122 and signal conditioning modules 124. However, in the embodiment of FIG. 1(b), the outputs of signal conditioning modules are received by a multi-channel ADC 152, which is in turn connected to a computer system 154 which receives and processes the digital signals produced by ADC 152. The digital signals may be transmitted via a wired or wireless (for example, Bluetooth or other RF communication standard) interface.

In the described embodiment, the computer system 154 may be a laptop or desktop computer system such as a 32-bit or 64-bit Intel Architecture-based computer system. The processes described below with reference to FIGS. 3 to 7 and executed by computer system 154 are implemented in the form of programming instructions of one or more software modules (including signal processing module 134) stored on non-volatile (e.g., hard disk) storage associated with the computer system 154. However, it will be apparent that at least parts of the processes described below with reference to FIGS. 3 to 7 could alternatively be implemented as one or more dedicated hardware components, such as application-specific integrated circuits (ASICs) and/or field programmable gate arrays (FPGAs).

The computer system 154 includes standard computer components, including random access memory (RAM), at least one processor, and external interfaces, all interconnected by a bus. The external interfaces include universal serial bus (USB) interfaces, at least one of which is connected to a keyboard and a pointing device such as a mouse, a network interface connector (NIC) which connects the system 154 to a communications network, and a display adapter, which is connected to a display device such as an LCD panel display. In addition to software modules 310-340, the system 154 may include further modules, for example a user interface module for displaying results generated by modules 310-340.

Referring now to FIG. 1(c), there is shown a further alternative embodiment of a system 170 in which the outputs of ADC 152 are transmitted to a cloud computing server 174. The system 170 may contain a computer system (not shown) to receive digital signals from ADC 152 and to transmit the signals to cloud computing server 174 via a wired or wireless interface 172. The computer system may be configured similarly to computer system 154 described above, except that modules 310-340 are instead stored on non-volatile memory of the cloud computing server 174, and cause one or more processors of cloud computing server 174 to execute the processes described below with reference to FIGS. 3 to 7. Multiple cloud computing servers 174 may collectively (e.g., in parallelized fashion) implement modules 310-340. The computer system may include a user interface module for interacting with cloud computing server(s) 174 and for displaying results of computations performed by server(s) 174.

Figure 2:
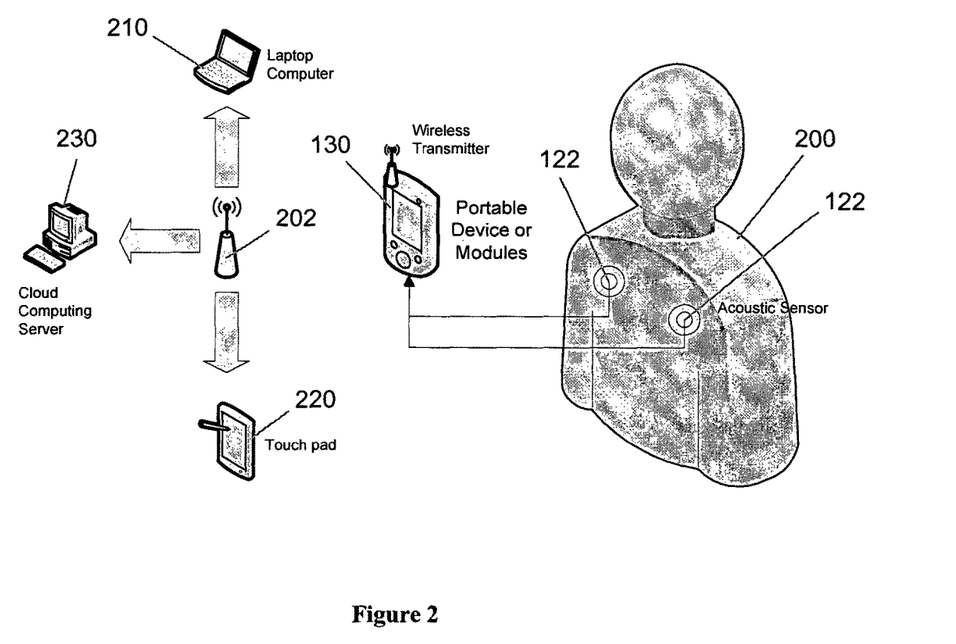
FIG. 2 schematically depicts one possible physical configuration of a system for detecting fluid accumulation.

FIG. 2 shows a sketch of possible physical configurations of the systems 100, 150, 170. Acoustic sensors 122 are attached to the chest of a patient 200 and are positioned near the patient's lungs such that they can record signals from acoustic pressure waves or sound generated from the lungs. Those signals are conditioned by passing them to filters/amplifiers 124 (not shown in the Figure), and the conditioned signal's are then transmitted (for example, wirelessly) to portable device 130. Processes executed or partly executed by modules 310-340 of FIG. 3 can then be carried out directly on portable device 130 to give an indication to the user of device 130 whether patient 200 has lung fluid accumulation. Alternatively, portable device 130 can delegate some or all of the processing to remotely located computing devices such as laptop computer 210 or cloud computing server 230, which communicate with portable device 130 via a wireless interface 202. Optionally, a further server (not shown) can be provided as an intermediary between portable device 130, laptop 210, cloud server 230 and other user devices, for example a tablet computer 220 which may be configured to receive and display the results of processes 300 as produced by laptop 210 or cloud server 230.

The detailed descriptions of the various modules 122, 124, 132 and 134 are described below.

Acoustic Sensor Module 122

The sensor 122 is an acoustic sensor which can be a stethoscope, a microphone, a piezo-electric device, a pressure sensor or any other device that can be used to record audio or audio generated signals. The system 100, 150 or 170 can operate with one or more sensors 122. For a multiple-sensor design, each of the sensors 122 is placed on a different part of the chest wall or back of the body. The multiple sensors 122 may be organized into two groups corresponding to the left and right lung positions respectively. Each sensor 122 may be connected to a signal conditioning module 124 and an ADC 132 or 152. The outputs of the ADC 132 or 152 are fed to a signal processing module 134.

Signal Conditioning Module 124 and ADC (Analog to Digital Converter) 132, 152

Each signal conditioning module 124 comprises a filter and an amplifier. The filter is configured to suppress out-of-band noise and interference. The amplifier is configured to amplify the power of the target signals within the band. The ADC 132 (or multi-channel ADC 152) converts the analog signals into digital signals so that they can be processed by digital signal processing techniques. The preferred specifications of the filter and amplifier module 124 and that for the ADC 132, 152 are given in Tables 1 and 2.

TABLE 1

Specification of the filter and amplifier module

| Design Parameters | Specifications |
|---|---|
| 1) Signal Bandwidth | 70 to 4000 Hz is recommended (possible values: 0 to 22.063 kHz) |
| 2) Attention of Stop-Band | 35 dB is recommended (possible values: 10 to 80 dB) |

TABLE 2

Specification of the ADC

| Design Parameters | Specifications |
|---|---|
| 1) Sampling Rate (Rs) | 8000 samples per second (sps) is recommended possible values: 1000 sps to 44.125 Ksps) |
| 2) Resolution | 12-bit to 16-bit is recommended (possible values: 8-bit to 32-bit) |

Signal Processing Module 134

Figure 3:
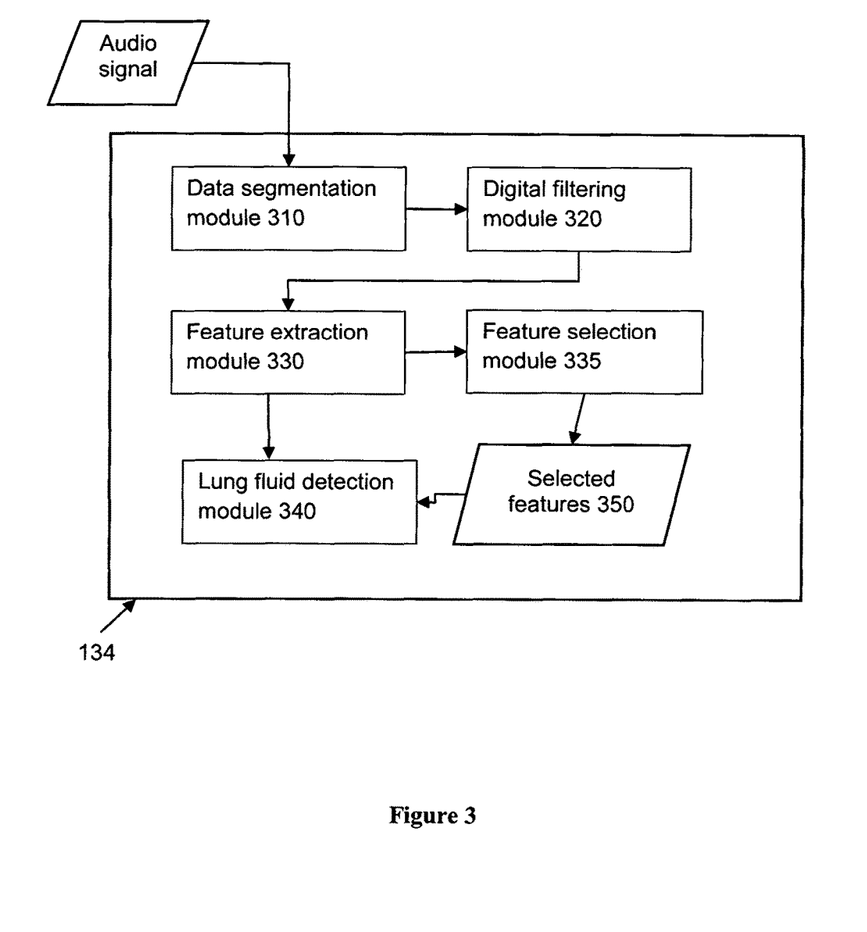
FIG. 3 is a block diagram of a signal processing module of a system according to embodiments of the invention.

A functional block diagram of the signal processing module 134 is shown in FIG. 3. Signal processing module 134 preferably has five sub-modules: (a) data segmentation module 310, (b) digital filtering module 320, (c) feature extraction module 330, (d) feature selection module 335, and (e) fluids detection module 340. The output of ADCs 132 or 152 is first divided into segments by segmentation module 310 so that sound signals can be processed continuously. A digital filter 320 is then used to remove some of the unwanted signals (e.g. noise and interference). A feature extraction method is applied by feature extraction module 330, to obtain a representation of the signal of interest (e.g., fluids in lung).

As not all the features (or parameters) extracted are useful, feature selection module 335 applies a feature selection method to select the useful features. In one example, the signal processing module 134 is operable in separate training and detection phases. During the training phase, as will later be described in more detail, feature selection module 335 receives feature vectors from multiple subjects and determines the most informative features (components of the feature vectors). The selected features 350 are stored and used as input to detection module 340 during the detection phase. For example, if selection module 335 determines that the $1^{st}$, $2^{nd}$ and $5^{th}$ features are of importance during the training phase, then during the detection phase when processing signals from a patient, those same components of the feature vector(s) for the patient are used by the fluids detection sub-module 340 to determine if fluids are present in the patient's lungs.

A flow chart of a process performed by signal processing module 134 and its sub-modules as discussed above is shown in FIG. 4. A detailed description of the process is given below.

Data Segmentation Sub-Module 310

Digitized sound samples received from ADCs 132 or 152 are stored in a buffer (memory), such as storage 136 of portable device 130, or non-volatile memory of computer system 154, continuously. These data are grouped into consecutive time-ordered segments of $N_w$ samples each, where the preferred value of $N_w$ ranges from 256 to 1024. Denote the duration of each segment as $T_w$, seconds. One example of the possible value of $T_w$ is 0.128 seconds, which corresponds to sampling 1024 samples when the sampling rate is 8,000 samples per second.

Figure 5:
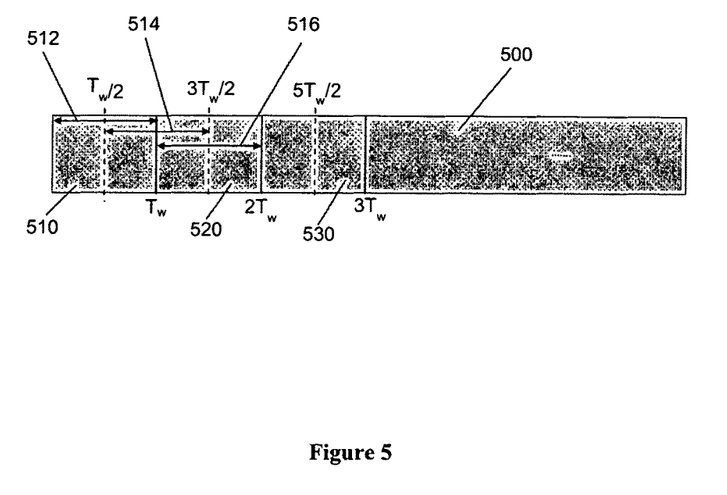
FIG. 5 is a schematic depiction of a data segmentation process.

As illustrated in FIG. 5, a sliding window is used to allow the same data to be used more than once. Advantageously, it has been found that allowing overlap between successive time windows increases the accuracy of lung fluid detection. In FIG. 5, a signal 500 has been segmented into segments 510, 520, 530 etc. (only the first three of which are shown), of width $T_w$. Windows 512, 514, 516 each of width $T_w$ and having 50% overlap with their immediate predecessor are derived from the signal 500. Accordingly, the first window 512 covers the first data segment 510; the second window 514 covers the time period from $T_w/2$ to $3T_w/2$ and overlaps with the second half of the first window 512; the third window 516 covers the time period from $T_w$ to $2T_w$ and overlaps with the second half of the second window 514; and so on. The amount of overlap between two consecutive windows can range from 0% to 100%, and the preferred value is 50%. As will be appreciated, a bigger percentage of overlap increases the accuracy but slows down the calculations. 50% is a good compromise which is widely used in digital signal processing techniques.

The windowed data derived from signal 500 are passed to feature extraction module 330, preferably via digital filtering module 320.

Digital Filtering Sub-Module 320

The digital filter module 320 is designed to provide a higher quality signal. Any digital filter known in the art and having the effect of suppressing noise and interference can be used here. The filter can be implemented as a FIR (Finite Impulse Response) filter or an UR (Infinite Impulse Response) filter.

Feature Extraction Sub-Module 330

For feature extraction, filtered data are first transformed into a feature vector of parameters. The feature vector advantageously provides a concise representation of the characteristics of the signals (e.g. acoustic signal produced by fluids in lung). The feature vector can be expressed as:

$$X=(x_1, x_s, \ldots, x_M),$$

where $x_1, x_s, \ldots,$ and $x_M$ are the values of the features (or parameters), and M is the number of features extracted. M is a user-defined parameter which is a number between 1 and the number of samples in one segment $N_w$. It has been found empirically that M between 10 and 15 is advantageous for analysis of lung sounds.

In general, m≥1 different feature-extraction schemes can be used. Two particular examples of feature extraction methods, which have advantageously been found to be useful with audio signals, are described below. However, it will be appreciated by the skilled person that a large number of feature extraction methods are possible. Other examples include Linear Prediction Coefficients and Wavelet transform based features. General dimensional reduction techniques may also be useful in some embodiments. One example of a feature extraction scheme is to use the Mel-Frequency Cepstral Coefficients (MFCCs) of the windowed signals as the element values $\{x_1\}$ of the feature vector. MFCC is performed for each segment (i.e. $N_w$ samples per segment) of the signal. Another exemplary feature extraction scheme uses the Perceptual Linear Prediction Coefficients (PLPCs) as the element values. The processes involved in determining these coefficients are summarized below.

Mel-Frequency Cepstral Coefficients (MFCCs).

The steps used to obtain the value of the MFCCs are as follows.
   a) Perform a Discrete Fourier Transform (DFT) of a windowed excerpt of the filtered signal 500 for each segment of signals
   b) Determine the power spectrum by squaring each of the DFT coefficients
   c) Map the power spectrum obtained onto the Mel scale using a triangular overlap window
   d) Perform a log transform of the power at each of the Mel frequencies
   e) Perform a Discrete Cosine Transform of the Mel log powers and take the amplitudes of the resulting spectrum as the MFCCs Preferred parameter values for deriving the MFCCs are as follows:
   a) M=13 typically
   b) Window size for the Fourier transform: 256 samples
   c) Size of the Fourier transform, $N_w$: 512 samples
   d) Number of linear filters: 13
   e) Linear frequency band inserted between neighboring filters: 66.66 Hz
   f) Lowest frequency of the filter: 133.33 Hz
   g) Number of log filters: 27
   h) Log space between log filters: 1.071

Perceptual Linear Prediction Coefficients (PLPCs)

Figure 6:
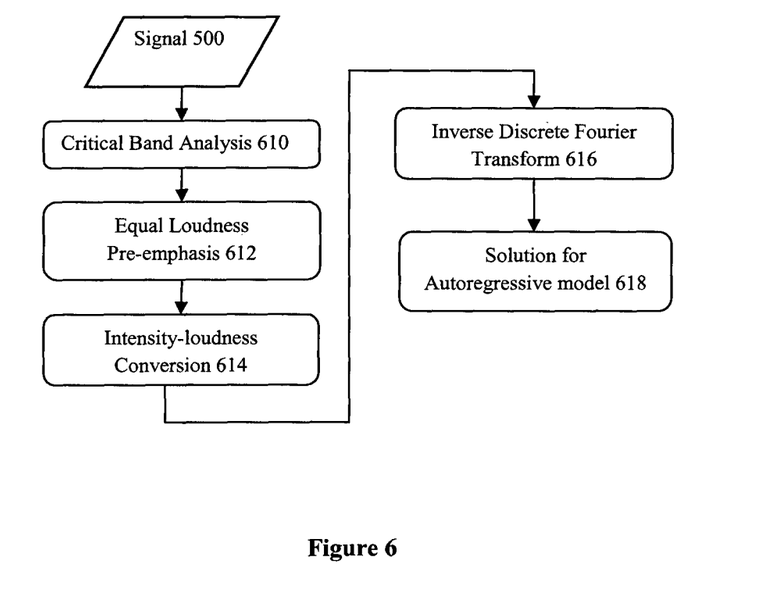
FIG. 6 is a flow chart of a process for determining perceptual linear prediction coefficients.

For this scheme, knowledge of the human hearing (perception) system is exploited in that, only the perceptually relevant details are extracted as the feature vector. The process is carried out in the frequency domain. A block diagram of the process is shown in FIG. 6. The process is summarized below.
   a) Perform a Discrete Fourier Transform (DFT) on the filtered signal for each segment of signals
   b) Determine the power spectrum by squaring each of the DFT coefficients
   c) Map the power spectrum obtained onto the PLPC scale using a trapezoidal overlap window (block 610)
   d) Perform an equal-loudness pre-emphasis (block 612) and intensity-to-loudness compression (block 614). This process effectively models both the warped frequency perception and the nonlinear and frequency-dependent human loudness perception.
   e) Perform a cube-root compression of the power at each of the frequencies
   f) Perform a Discrete Cosine Transform of the cube-root powers and take the amplitudes of the resulting spectrum
   g) Transform the signals back to the time domain by performing an inverse Fourier transform (block 616).
   h) Perform a regular linear prediction analysis and take the resultant coefficients as the PLPCs (block 618).

The preferred order of PLP is 10 (the possible values can range from 1 to NO. The value of M is typically 11, and is preferably in the range 10 to 15 as outlined above.

Feature Selection 335

Not all of the features extracted may be of high relevance to the characteristics of the target signals (i.e. fluids). For this reason, a subset of the features extracted above may be selected and used in the decision making module 340. The selection process is implemented by selection module 335 and takes training data, in which a plurality of patient samples are pre-labeled with a class (e.g. presence or absence of lung fluid, or different amounts of lung fluid). The features selected by the feature selection process (stored as selected feature data 350) can then be used by the detection module 340 to determine if fluid is present, and optionally to determine the degree to which it is present. The training process is described in more detail later.

In preferred embodiments, the feature selection process selects features from the feature vector based on their importance. Importance is defined as the ratio of the sum of squared inter-class divergence to the sum of intra-class spread:

$$I(x_i) = \frac{\sum_{j \neq k}(m_{i,c(j)} - m_{i,c(k)})^2}{\sum_{c(j)} \sigma^2_{i,c(j)}} \quad (i = 1, 2, \ldots, M), \quad [1]$$

where $m_{i,c(j)}$ and $\sigma_{i,c(j)}^2$ are the sample mean and variance of the feature $x_i$ for the class $c(j)$ respectively, and $c(j)$, $j=1, 2, \ldots N_c$ is the $j^{th}$ class. The number of classes, $N_c$, is the number of levels corresponding to different amounts of fluid and can be pre-determined by the user (e.g. 0 means absence of fluid, 1 means a small amount of fluid, 2 means more fluid, and so on). The larger the value of $I(x_i)$, the more important the feature $x_i$ is. In the special case where the objective is to determine the presence or absence of water in lung, it becomes a 2-class problem where $N_c=2$, and $c(1)=1$ and $c(2)=-1$. Those skilled in the art will appreciate that the methods described herein may be readily modified or extended to cover any number of classes (e.g. corresponding to different levels of lung fluid).

Feature selection module 335 selects the $N \leq M$ number of features with the largest values of $I(x_i)$, to form the resultant (selected) feature vector $Y=(y_1, y_2, \ldots y_N)$. The preferred values of N are between 4 and 8 for MFCCs and between 7 and 11 for PLPCs.

In the case where multiple feature extraction schemes are used, all the features selected (by the various feature extraction schemes) can be considered together, and the same feature selection process described above may be applied.

Fluids Detection Sub-Module 340

Figure 7:
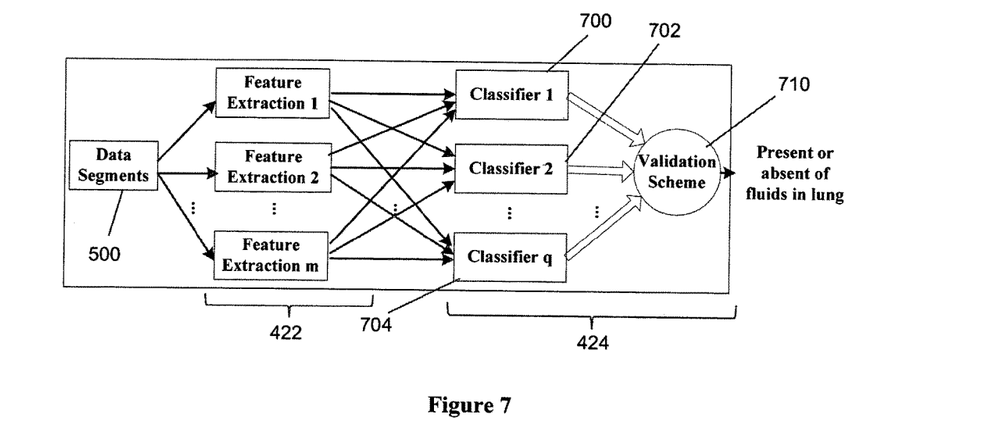
FIG. 7 is a block diagram showing components of a multi-feature extraction multi-classifier signal processing module.

A block diagram of an exemplary feature extraction and fluid detection process 422, 424 is shown in FIG. 7. The fluid detection process comprises implementing a bank of $q \geq 1$ classifiers 700, 702, ..., 704, followed by a validation process 710. The function of each classifier 700-704 is to tentatively determine the class to which the received feature vector Y (provided by feature extraction process or processes 422) belongs. The final decision on which class the feature vector belongs to is determined by the subsequent validation process 710. One special case of this design is to use one (q=1) classifier (instead of a bank of more than one classifier) and a simpler validation scheme.

Classifiers 700 to 704

Each of the q classifiers 700 to 704 may be a binary-class classifier. It will be appreciated that the design of the described embodiments can be readily extended to a multiple-class classifier design. In a binary-class classifier, the objective is to determine if fluid is present or absent in the lung of a patient for whom measured audio signals result in a feature vector Y generated by feature extraction/selection module 330 as described above, and the two classes are $c(1)$ and $c(2)$ respectively, where $c(1)=1$ (presence of fluid) and $c(2)=-1$ (absence of fluid).

Preferred embodiments provide two methods of tentatively determining the class to which the received feature vector Y belongs. A wide variety of other methods are also applicable, including neural network-based methods, support vector machines, extreme learning machines, and so on.

a) The first method is a linear classification method. A vector $\varphi(Y)$ is first determined using the following equation $$\varphi(Y) = w^T Y + b, \quad [2]$$

where $w^T = (w_1, w_2, \ldots w_N)$ is a vector and b is a scalar value. The value of $w^T Y$ can be calculated as follows:

$$w^T Y = \sum_{i=1}^{N} w_i y_i. \quad [2a]$$

If the fluid detection module 340 is implemented in hardware, Equation [2a] is readily implemented using N multipliers and adders.

The values of w and b are pre-determined, during the training phase which will be explained later. The process above can be repeated for different numbers N of selected features. The recommended values are N=4, 5, 6, 7, 8 when MFCCs are used and N=7, 8, 9, 10, 11 when PLPCs are used. The corresponding w and b are given in Table 3.

For each of w and b considered, Y is determined tentatively to be in class $c(1)$ (i.e. fluid is present) if $\varphi(Y)>0$, or in class $c(2)$ (i.e. fluid is absent) otherwise.

b) The second method is a nonlinear method which is "Euclidean distance" based. Other distance metrics are of course possible. In this method, the Euclidean distances between the received feature vector Y and the feature vectors obtained during the training phase (denoted as $\{\overline{Y}_i\}$) are first determined. The $\{\overline{Y}_i\}$ corresponding to the k shortest distances and the corresponding classes they belong to, $\{\overline{c}_{Y_i}\}$, are identified. The received feature vector Y is tentatively determined to be in class $c(1)$ (i.e. fluids is present) if there are more $c(1)$ than $c(2)$ in $\{\overline{c}_{Y_i}\}$. Otherwise, Y will be tentatively determined to be in class $c(2)$ (i.e. fluids is absent). The preferred value of k is 3 but it can also take on other integer values larger than 3.

The classifiers used in detection module 340 may be a series of linear classifiers, a series of non-linear classifiers, or a combination of the two.

As shown in FIG. 7, the classification processes 700 to 704 may be repeated for each of the feature extraction methods 422 implemented by feature extraction module 330.

So, for example, if MFCC and PLPC feature, extraction are both used, and if q=3, then the two feature vectors generated by the MFCC and PLPC methods respectively will be processed by each one of the 3 classifiers 700 to 704, to generate a total of 2×3=6 tentative classification outcomes.

TABLE 3

| | | Preferred sets of values for w and b | |
|---|---|---|---|
| | N | w | b |
| MFCCs | 4 | (0.3879, 0.0553, 0.0299, −0.0030) | 10.5166 |
| | 5 | (0.3895, 0.0554, 0.0304, −0.0032, 0.0193) | 10.5643 |
| | 6 | (0.3889, 0.0554, 0.0302, −0.0031, 0.0193, −0.0043) | 10.5493 |
| | 7 | (0,3868, 0.0552, 0,0315, −0.0032, 0,0203, −0.0030, 0.0374) | 10.4681 |
| | 8 | (0.3869, 0.0552, 0.0316, −0.0032, 0.0203, −0,0030, 0.0374, 0.0185) | 10.4713 |
| PLPCs | 7 | (1.0693, 0.2127, 0.0684, 0.0300, 0.0580, −0.0214, −0.0830) | −3.7728 |
| | 8 | (1.0693, 0.2127, 0.0684, 0.0300, 0.0580, −0.0214, −0.0830, −0,0080) | −3.7728 |
| | 9 | (1.0693, 0.2127, 0.0684, 0.0300, 0.0580, −0.0214, −0.0830, −0,0080, 0.0015) | −3.7727 |
| | 10 | (1.0693, 0.2127, 0.0684, 0.0300, 0.0580, −0.0214, −0.0830, −0,0080, 0.0015, −0.0094) | −3.7743 |
| | 11 | (1.0693, 0.2127, 0.0684, 0.0300, 0.0580, −0.0214, −0.0830, −0,0080, 0.0015, −0.0094, 0.0243) | −3.7715 |

Validation Process 710

In validation process 710, several consecutive tentative classification outcomes, as generated by classifiers 700 to 704, are used to confirm the decision on the class to which the received feature vector Y belongs to. The process is preferably as described below.

Consider $N_m$ concurrent received feature vectors $\{Y_i\}$, i=1, 2, ... $N_m$, where m is the number of different types of feature vector (e.g., m=2 if one MFCC and one PLPC feature extraction is performed). Let the validation duration be denoted as $T_m$ seconds and the corresponding number of feature vectors be denoted as $N_{T_m}$, where $N_{T_m} \geq N_m$ ($N_{T_m} = N_m \times$ q).

If all the classes determined by a classifier for $\{Y_i\}$, i=1, 2, ... $N_m$ are the same, then the signal 500 is determined to be in that class. If this condition is not met, then the signal 500 will be determined to be in the class that has been determined to occur the most number of times among the $\{Y_i\}$, i=1, 2, ... $N_{T_m}$.

Training Process

Figure 4:
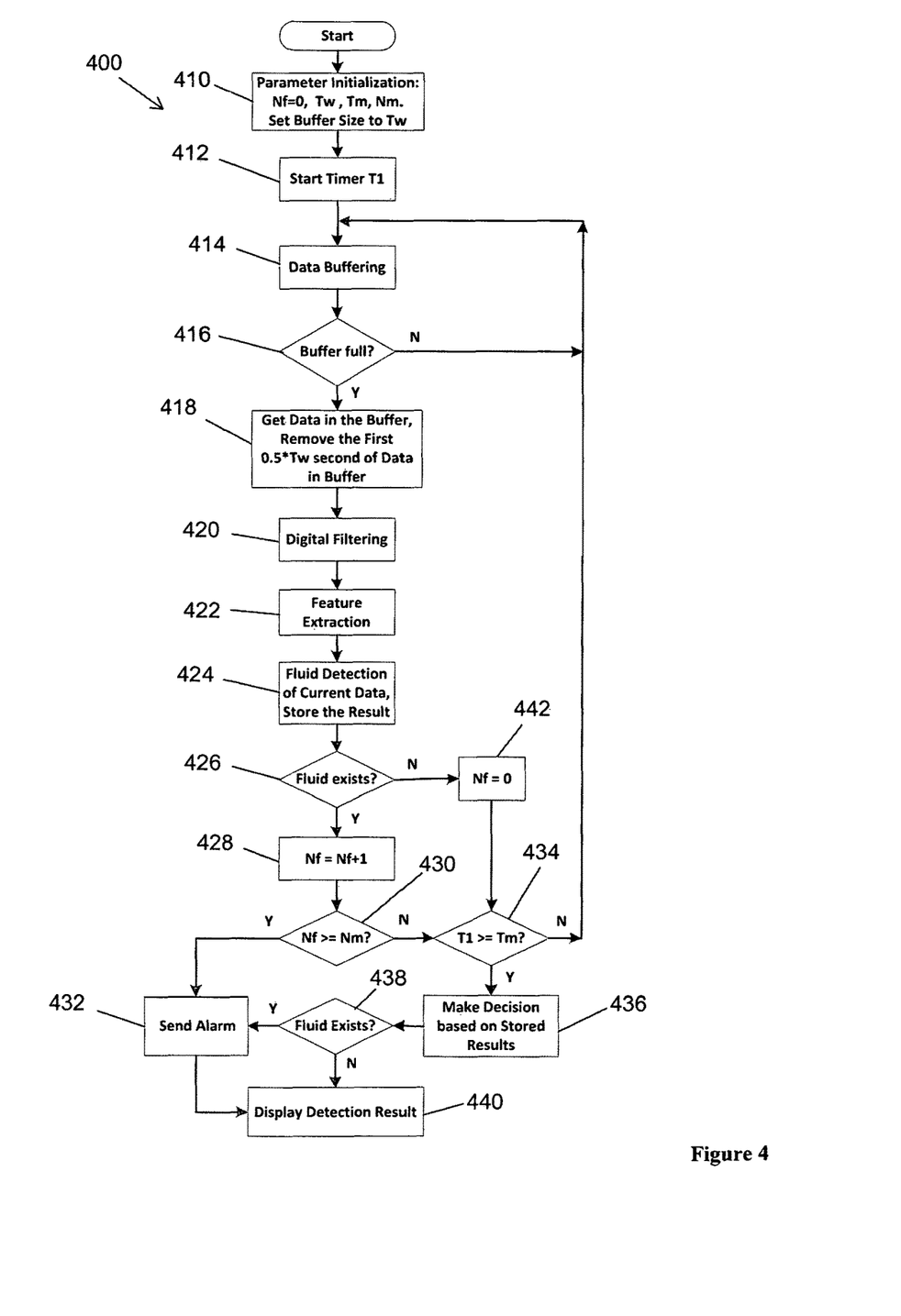
FIG. 4 is a flow chart of a method according to embodiments of the invention.

Prior to the use of the fluids detection module 340 and process 424 described above, a large number of samples of lung sounds (with fluids and without fluids, or with varying levels of fluid—e.g. none, low, medium, high) are collected to form a training data set. A training process will then be performed on this data set to determine the vectors w and scalar b of Equation[2]. The parameters w and b will then be stored, for example on storage 136 or on non-volatile storage of computer system 154 or cloud computing server 174, for retrieval by fluid detection module 340 and lung fluid for the detection process 424 later.

An exemplary method of training a linear classifier to distinguish between different levels of lung fluid is as follows:

a) Record a large amount of acoustic data across different human subjects, where each set of data for each subject is tagged with a class according to the ground truth (i.e. a class which is based on an independent measurement of the subject, using e.g. X-ray or CT scan data).

b) Extract (by feature extraction module 330) and select (by feature selection module 335) $N_\infty$ feature vectors from these data and denote them as $\{\overline{Y}_j\}$, j=1, 2, ... $N_\infty$, where $N_\infty$ is a very large integer value and $\overline{Y}_j = (\overline{y}_1, \overline{y}_2, \ldots \overline{y}_n)_j$. The corresponding classes $\{\overline{c}_{y_j}\}$ for these vectors are as specified by the ground truth from step a).

c) w and b are then determined as follows.

$$w = \sum_{j=1}^{N_\infty} \alpha_j \times \overline{c}_{Y_j} \times \overline{Y}_j \quad [3]$$

$$b = \overline{c}_{Y_j} - w^T \overline{Y}_j \quad \text{for any } j \text{ with } \alpha_j > 0 \quad [4]$$

The values of $\alpha_i$ are selected in the following way. First define $L(\alpha)$ as:

$$L(\alpha) = \sum_{i=1}^{N_\infty} \alpha_i - \frac{1}{2} \sum_{i=1}^{N_\infty} \sum_{j=1}^{N_\infty} \alpha_i \alpha_j \overline{c}_{Y_i} \overline{c}_{Y_j} Y_i^T Y_j \quad [5]$$

The values of $\alpha_i$, i=1, 2, ... N are selected to maximize $L(\alpha)$ subject to the following constraints:

$$\sum_{i=1}^{N} \alpha_i \overline{c}_{Y_i} = 0; \text{ and} \quad [6]$$

$$0 \leq \alpha_i \leq \tilde{C}, \quad [7]$$

where $\tilde{C}$ is a constant. The preferred value of $\tilde{C}$ is 0.01 but it can take on any non-negative values. There are several ways to find the values of $\alpha_i$ such that $L(\alpha)$ is the largest. One way is to solve Equations [5]-[7] via the well known QP (Quadratic Programming) problem.

Exemplary Detection Process 400

An example of a detection process 400 will now be described, with reference to FIG. 4. The overall control of process 400 is executed by signal processing module 134, with various steps within the process being performed by one or more of sub-modules 310, 320, 330 and 340.

At block 410, parameters for the detection process 400 are initialized. In particular, a counter index $N_f$ is first set to zero. The width of a time window, $T_w$, in seconds is set as mentioned above. Parameters $N_m$ and $T_m$ for the validation process 710 are also set as mentioned above.

At block 412, a clock is started, and data buffering begins at block 414. If the check at block 416 determines that the buffer is full, the first $0.5 \ast T_w$ seconds of data are cleared from the buffer (block 418). Filtering is performed (block 420) on the buffered data, by digital filter module 320, and the filtered data are then passed to feature extraction module 330 (block 422). Feature extraction module 330 extracts feature vectors as described above. Features selected using selection module 335, during the training phase, are then used in the detection process 424.

Fluids detection sub-module 340 performs detection process 424 substantially as described above, and stores the result of each detection. If a positive detection occurs then Nf is increased by 1 at block 428 and we proceed to block 430. Otherwise, Nf is reset to zero at block 442 and the signal processing module 134 checks at block 434 on whether the clock time is equal to or greater than $T_m$. If so, a decision is made based on all previously stored detection results at block 436, and displayed at block 440. A decision that fluid is present (block 438) results in generation of an alarm signal at block 432, prior to displaying a positive result at block 440.

Returning to block 430, if Nf equals or exceeds the maximum number of positive detections Nm, an alarm signal is generated at block 432 and the detection result is displayed (for example on display 138) at block 440. If not, and the clock is at less than Tm seconds, we return to block 414 to get the next block of data. If the clock is at Tm or greater, then a decision is made based on previously stored results (block 436). If the decision is that fluid is present (block 438) then the alarm signal is generated and the positive result displayed as before. Otherwise, a negative result is displayed at 440.

Classification Accuracy

Figure 8:
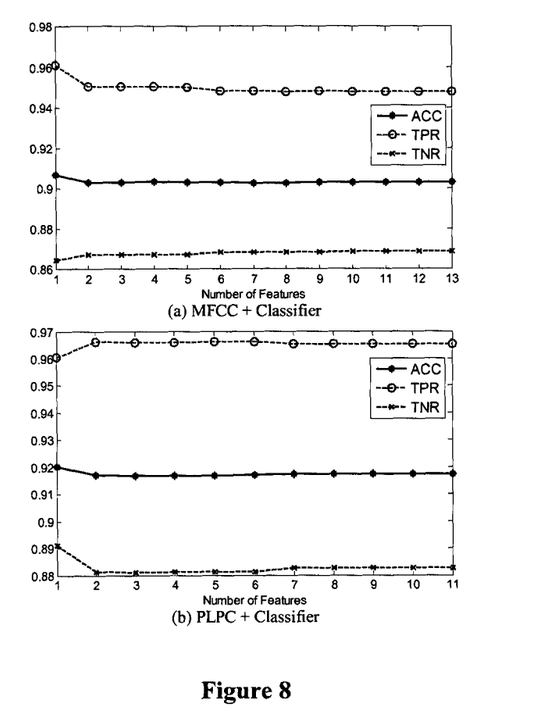
FIG. 8 shows results of classification accuracy for methods according to embodiments of the invention.

Referring to FIG. 8, classification results from testing of embodiments of the method are shown.

In FIG. 8(a), the solid line with data points plotted with asterisks shows the accuracy (ACC) of the method, as a function of the number of features per feature vector, when using MFCCs for feature extraction with the linear classifier defined by Equation [2]. The upper dashed line plotted with circles shows the true positive rate (TPR), and the lower dashed line plotted with crosses shows the true negative rate (TNR). As can be seen, as few as 1 or 2 features can be used to obtain classification accuracy of 90% or better, a TPR of 95% or better, and a TNR of 86% or better.

Similarly, in FIG. 8(b), results for the classification when using PLPCs for feature extraction are shown. Slightly superior results are obtained when using PLPCs. An accuracy of 92% or better, a TPR of 0.96% or better and a TNR of 88% or better are obtained regardless of the number of features extracted per feature vector.

Preferred Designs of the Portable Device, Sensor-Computer, Sensor-Cloud Computing Configurations In the portable device configuration 100, the detection of fluids in lung is performed by the signal processing module 134 installed in the portable device 130. The results can be stored in a memory 136 (e.g. Micro SD card) and/or can be displayed on the portable device 130. At least one sensor is required, but more sensors can be used, depending on the size and shape of the device design.

For the sensor-computer configuration 150, the sensor module(s) 122 and the signal conditioning module(s) 124 may be housed together. The output of the signal conditioning module may be fed to a computer 154 either by wire or through the use of a wireless interface (e.g. Bluetooth). A multi-channel ADC 152 can be used in conjunction with the computer 154 and the signal processing is performed in the computer 154 by a signal processing module having similar functionality to signal processing module 134.

The design of the sensor-cloud computing configuration 170 is similar to that of the sensor-computer configuration 150 except that the ADC 152 is now collocated with the sensor and signal conditioning modules 122, 124 and that the signal processing is done in a cloud computing server 174 instead of a laptop or desktop computer 154.

Although particular embodiments of the invention have been described in detail, many variations are possible within the scope of the invention, as will be clear to a skilled reader.

The invention claimed is:

1. A method of detecting a level of fluid accumulation in a lung of a subject, comprising:
   providing at least one classifier trained to distinguish between two or more levels of fluid accumulation, the two or more levels comprising a level corresponding to a presence of fluid and a level corresponding to an absence of fluid;
   acquiring an audio signal generated by the lung;
   processing said audio signal by:
      segmenting the audio signal into consecutive time windows;
      performing feature extraction to generate at least one feature vector for each time window; and
      assigning a level of fluid accumulation from the two or more levels to the audio signal by:
         passing at least one component of each feature vector to the at least one classifier to generate a plurality of tentative fluid levels for the audio signal; and
         selecting a most frequent occurring level from amongst the plurality of tentative fluid levels; and
   providing an indication to a user that the subject has lung fluid accumulation if the most frequent occurring level is the level corresponding to the presence of fluid.

2. A method according to claim 1, wherein said consecutive time windows at least partially overlap.

3. A method according to claim 1, wherein the passing at least one component of each feature vector to the at least one classifier comprises passing selected components of each feature vector to the at least one classifier.

4. A method according to claim 3, wherein performing the feature extraction comprises determining mel-frequency cepstral coefficients or determining perceptual linear prediction coefficients, or both.

5. A method according to claim 4, wherein determining the mel-frequency cepstral coefficients comprises selecting between 4 to 8 components.

6. A method according to claim 4, wherein determining the perceptual linear prediction coefficients comprises selecting between 7 to 11 components.

7. A method according to claim 1, wherein the at least one classifier comprises at least one linear classifier.

8. A method according to claim 1, wherein the at least one classifier comprises at least one non-linear classifier.

9. A method according to claim 1, further comprising training the at least one classifier.

10. A method according to claim 9, wherein said training comprises:
   acquiring audio signals from a plurality of subjects having known levels of fluid accumulation;
   performing feature extraction on the audio signals acquired from the plurality of subjects having known levels of fluid accumulation to generate a plurality of candidate feature vectors; and
   performing feature selection on the plurality of candidate feature vectors to identify one or more components of the candidate feature vectors which are useful for discriminating between the two or more levels.

11. A method according to claim 10, wherein the feature selection is performed by identifying N features having greatest importance, from the plurality of candidate feature vectors and wherein an importance of a feature is calculated according to:

$$I(x_i) = \frac{\sum_{j \neq k} (m_{i,c(j)} - m_{i,c(k)})^2}{\sum_{c(j)} \sigma^2_{i,c(j)}},$$

where $i=1, \ldots, M$; M is a dimension of each candidate feature vector; $m_{i,c(j)}$ and $\sigma^2_{i,c(j)}$ are a sample mean and a variance, respectively, of a feature $x_i$ for a class $c(j)$; $c(j)$, $j=1, 2, \ldots N_c$ is a $j^{th}$ class; and $N_c$ is a number of levels of fluid accumulation.

12. A method according to claim 11, wherein M ranges from 10 to 15.

13. A method according to claim 1, wherein said acquiring comprises positioning at least one sensor on the subject in proximity to the lung such that the sensor is acoustically coupled to the lung.

14. A method according to claim 1, wherein the indication comprises an alarm signal.

15. A method according to claim 1, wherein said acquiring comprises acquiring the audio signals using a plurality of audio sensors.

16. A method according to claim 15, wherein said acquiring comprises positioning the plurality of audio sensors on the subject in proximity to the lung such that each of the sensors is coupled to the lung.

17. A system for detecting a level of fluid accumulation in a lung of a subject, comprising:
   at least one sensor positionable on the subject adjacent the lung to measure an audio signal generated by the lung;
   a memory configured to store data representing the audio signal; and at least one processor in communication with the memory and being configured to:

retrieve, from said memory, data representing at least one classifier trained to distinguish between two or more levels of fluid accumulation, the two or more levels comprising a level corresponding to a presence of fluid and a level corresponding to an absence of fluid;

process said audio signal by segmenting the audio signal into consecutive time windows, and performing feature extraction to generate at least one feature vector for each time window;

assign a level of fluid accumulation from the two or more levels to the audio signal by:
 passing at least one component of each feature vector to the at least one classifier to generate a plurality of tentative fluid levels for the audio signal; and
 selecting a most frequent occurring level from amongst the plurality of tentative fluid levels; and provide an indication to a user that the subject has lung fluid accumulation if the most frequent occurring level is the level corresponding to the presence of fluid.

18. A system according to claim 17 wherein the indication comprises an alarm signal.

19. A system for detecting a level of fluid accumulation in a lung of a subject, comprising:

at least one sensor positionable on the subject adjacent the lung to measure an audio signal generated by the lung; and at least one processor configured to:

segment the audio signal into consecutive time windows;

perform feature extraction to generate at least one feature vector for each time window;

assign to each time window a fluid level which is one of a set of two or more levels of fluid accumulation by passing at least one component of the at least one feature vector for each time window to at least one classifier trained to distinguish between the two or more levels of fluid accumulation to generate a plurality of tentative fluid levels for the audio signal, wherein the two or more levels comprises a level corresponding to a presence of fluid and a level corresponding to an absence of fluid;

select a most frequent occurring level from amongst the plurality of tentative fluid levels and provide an indication to a user that the subject has lung fluid accumulation if the most frequent occurring level is the level corresponding to the presence of fluid.

20. A system according to claim 19 wherein the indication comprises an alarm signal.

* * * * *

UNITED STATES PATENT AND TRADEMARK OFFICE
CERTIFICATE OF CORRECTION

PATENT NO.        : 10,368,804 B2                           Page 1 of 1
APPLICATION NO.   : 14/421505
DATED             : August 6, 2019
INVENTOR(S)       : Wee Ser, Feng Yang and Jufeng Yu It is certified that error appears in the above-identified patent and that said Letters Patent is hereby corrected as shown below:

On the Title Page

Item (72) Inventors: Correct the third inventor's name from "Junfeng Yu" to --Jufeng Yu--.

Signed and Sealed this
Twenty-second Day of September, 2020

Andrei Iancu
*Director of the United States Patent and Trademark Office*